(12) United States Patent
Strebelle et al.

(10) Patent No.: US 7,863,211 B2
(45) Date of Patent: *Jan. 4, 2011

(54) EPOXIDATION CATALYST, ITS USE AND EPOXIDATION PROCESS IN THE PRESENCE OF THIS CATALYST

(75) Inventors: Michel Strebelle, Brussels (BE); Jean-Pierre Catinat, Waudrez (BE)

(73) Assignee: Solvay SA, Brussels (BE)

( * ) Notice: Subject to any disclaimer, the term of this patent is extended or adjusted under 35 U.S.C. 154(b) by 1273 days.

This patent is subject to a terminal disclaimer.

(21) Appl. No.: 10/790,023

(22) Filed: Mar. 2, 2004

(65) Prior Publication Data

US 2004/0167342 A1    Aug. 26, 2004

(51) Int. Cl.
*B01J 29/89* (2006.01)
(52) U.S. Cl. .............................. 502/64; 502/60; 502/71; 502/423
(58) Field of Classification Search .................. 502/423, 502/60, 71, 64, 77
See application file for complete search history.

(56) References Cited

U.S. PATENT DOCUMENTS

| | | | | |
|---|---|---|---|---|
| 4,613,427 A | * | 9/1986 | Sepulveda et al. | ..... 208/111.15 |
| 5,965,476 A | * | 10/1999 | Balducci et al. | ............... 502/67 |
| 6,458,970 B1 | * | 10/2002 | Hefele et al. | ................. 549/247 |

FOREIGN PATENT DOCUMENTS

DE    19623611    * 12/1997

* cited by examiner

*Primary Examiner*—Kevin P Kerns
*Assistant Examiner*—Devang R Patel
(74) *Attorney, Agent, or Firm*—Stites & Harbison PLLC; B. Aaron Schulman; Stephen J. Weyer

(57) ABSTRACT

Epoxidation catalyst based on titanium zeolite in the form of extruded granules. Use of this catalyst in the synthesis of epoxides, preferably 1,2-epoxy-3-chloropropane or 1,2-epoxypropane, by reacting an olefinic compound, preferably allyl chloride or propylene, with a peroxide compound, preferably hydrogen peroxide. Process for the preparation of an epoxide, preferably 1,2-epoxy-3-chloropropane or 1,2-epoxypropane, by reacting an olefinic compound, preferably allyl chloride or propylene, with a peroxide compound, preferably hydrogen peroxide, in the presence of the aforementioned catalyst.

16 Claims, No Drawings

EPOXIDATION CATALYST, ITS USE AND EPOXIDATION PROCESS IN THE PRESENCE OF THIS CATALYST

This application is a divisional of U.S. patent application Ser. No. 09/555,149, filed May 26, 2000.

The present invention relates to epoxidation catalysts, in particular catalysts based on titanium zeolite. It also relates to the use of these catalysts in epoxidation reactions, as well as to epoxidation processes in the presence of these catalysts.

It is known to use catalysts based on titanium silicalite in epoxidation reactions. For example, in patent application EP-A2-0 200 260, microspheres based on titanium silicalite which have a diameter of about 20 µm and are obtained by atomization, are used in epoxidation reactions. This known catalyst gives rise to a deactivation phenomenon. Regeneration cycles, requiring handling operations, are therefore necessary. When these catalysts, with a relatively small diameter, are used in epoxidation reactions it is difficult to isolate them from the reaction medium so that they can be transferred to a regeneration treatment.

The object of the present invention is to resolve this problem by providing a novel catalyst which is easy to separate from the epoxidation reaction medium with a view to sending it to a regeneration unit. A further object of the invention is to provide an epoxidation catalyst which has good mechanical strength, high catalytic activity and high selectivity.

Yet another object of the invention is to provide a catalyst which is easy to use in a fixed or fluidized bed.

The present invention therefore relates to an epoxidation catalyst based on titanium zeolite, which is in the form of extruded granules. It has been found that such a catalyst has the following combined advantages:

it is easy to separate from the epoxidation reaction medium with a view to sending it to a regeneration unit,
it has good mechanical strength, high catalytic activity and high selectivity,
it is easy to use in a fixed or fluidized bed.

The term titanium zeolite is intended to mean a solid containing silica which has a microporous crystalline structure of the zeolite type and in which a plurality of silicon atoms are replaced by titanium atoms.

The titanium zeolite advantageously has a crystalline structure of the ZSM-5, ZSM-11 or MCM-41 type. It may also have a crystalline structure of the aluminium-free β zeolite type. It preferably has an infrared absorption band at about 950-960 cm$^{-1}$. Titanium zeolites of the silicalite type are highly suitable. Those satisfying the formula $xTiO_2(1-x)SiO_2$ in which x is from 0.0001 to 0.5, preferably from 0.001 to 0.05, give good performance. Materials of this type, known by the name TS-1, have a microporous crystalline zeolite structure similar to that of the ZSM-5 zeolite. The properties and main applications of these compounds are known (B. Notari; Structure-Activity and Selectivity Relationship in Heterogeneous Catalysis; R. K. Grasselli and A. W. Sleight Editors, Elsevier: 1991; p. 243-256). Their synthesis has been studied, in particular by A. Van der Poel and J. Van Hooff (Applied Catalysis A, 1992; Volume 92, pages 93-111). Other materials of this tope haste a structure similar to that of beta zeolite or ZSN-11 zeolite.

The term extruded granules is intended to mean grains obtained by extrusion. In particular, the granules are obtained by extruding an extrudable mass containing the titanium zeolite and by cutting the extrudate emerging from the extruder into grains.

The shape of the extruded granules is arbitrary. They may be solid or hollow. They may be of round or rectangular cross-section, or alternatively a different cross-section with a greater external surface area. Cylindrical shapes are preferred. When they are of cylindrical shape, the extruded granules advantageously have a diameter of at least 0,5 mm, preferably of at least 1 mm. The diameter is usually at most 5 mm, particularly at most 2 mm. The cylindrical shapes have usually a length of at least 1 mm, particularly of at least 2 mm. Lengths of at most 8 mm are current, those of at most 4 mm give good results. The cylindrical shapes having a diameter of from 0.5 to 5 mm, preferably from 1 to 2 mm, and a length of from 1 to 8 mm, preferably from 2 to 4 mm are suitable.

The content of titanium zeolite in the catalyst according to the invention is generally at least 1% by weight, in particular at least 50% by weight. The content of titanium zeolite is most often at most 99% by weight, particularly at most 98% by weight. The catalyst according to the invention generally contains from 1 to 99% by weight, preferably from 50 to 98% by weight, of titanium zeolite, the remainder consisting of a matrix. This matrix preferably contains a siliceous material.

The catalyst according to the invention can be obtained by a process comprising:

(a) a step of blending a mixture comprising a titanium zeolite powder, water, at least one binder, at least one plasticizer and optionally other additives, in order to form a paste,
(b) a step of shaping the paste obtained in step (a) by extrusion, in order to obtain an extrudate,
(c) a step of drying in order to remove at least some of the water,
(d) a step of calcining in order to remove at least some of the organic residues present, and comprising a granulation step carried out between the extrusion step (b) and the drying step (c) or after the calcining step (d), in order to obtain extruded granules.

Step (a) generally consists in mixing a titanium zeolite powder with water, at least one binder, at least one plasticizer and optionally other additives until a paste is obtained with a viscosity such that it can be employed in an extruder. The mixing may be carried out in any kind of mixer or blender. All the constituents of the mixture can be mixed simultaneously. As a variant, the binder, the plasticizer, the water and, if appropriate, the other additives may be premixed before they are added to the titanium zeolite powder. The mixing is advantageously carried out at room temperature. As a variant, the mixture may be cooled during step (a), for example with water. The duration of step (a) can vary from 5 to 60 minutes.

The particle size distribution of the titanium zeolite powder employed in step (a) can vary greatly. It is preferably characterized by a mean diameter of less than or equal to 10 µm, in particular less than or equal to 5 µm. The mean diameter is generally at least 0.05 µm, in particular at least 0.1 µm. Diameters of less than 0.05 µm are also suitable.

The plasticizer which can be used in step (a) may be a polysaccharide such as a starch or a cellulose. Celluloses are highly suitable. By way of examples of cellulose, mention may be made of methyl cellulose, carboxymethyl cellulose and hydroxyethyl cellulose. Methyl cellulose is preferred.

The amount of placticizer employed in step (a) can vary greatly. Small amounts of at least 1% and less than 10% by weight relative to the weight of titanium zeolite employed are recommended because they lead to better resistance to attrition in comparison with higher amounts.

The binder which can be used in step (a) may be selected from silicon derivatives such as siloxanes. By way of examples, mention may be made of methyl siloxane or ethyl siloxane ethers. Silicone resins based on polymethylsiloxane may also be used. Silicone resins of the polymethyl/phenylsiloxane type are also suitable. It is also possible to use mixtures of different oligomers of the methylsiloxane type.

The binder employed in step (a) may be in the form of a powder. As a variant, it may be in the form of an aqueous emulsion. It may also be used in liquid form. Silicone resins based on polymethylsiloxane in the form of a powder, and mixtures of different oligomers of the methylsiloxane type in liquid form are preferred because they lead to catalysts with higher mechanical strength. In the calcining step (d), the binder is converted into a material forming the matrix which is present in the catalyst according to the invention.

The amount of binder employed in step (a) can vary greatly. It is customarily at least 3% by weight, in particular at least 5% by weight, relative to the weight of titanium zeolite employed. It is commonly at most 70% by weight, in particular at most 30% by weight, relative to the weight of titanium zeolite employed. Amounts of from 5 to 20% by weight relative to the weight of titanium zeolite employed are particularly highly suitable because they lead to a better compromise between the catalytic activity and the mechanical strength in comparison with lower or higher amounts.

Lubricators may also be added to the mixture of step (a). These may be compounds based on paraffin, polyvinylpyrrolidone, polyethylene oxide and polyvinyl alcohol.

Pore-forming substances may also be added to the mixture of step (a). These substances are removed during the calcining step (d) and thus increase the porosity of the catalyst. Melamine may be mentioned by way of an example of a pore-forming substance. The amount of pore-forming substance employed is generally at least 5% by weight, in particular at least 6% by weight, relative to the weight of titanium zeolite employed. It is customarily at most 35% by weight, in particular at most 14% by weight, relative to the weight of titanium zeolite employed. Amounts of from 6 to 14% by weight relative to the weight of titanium zeolite employed are particularly suitable because they lead to better resistance to attrition in comparison with higher amounts.

The extrusion step (b) may be carried out in a piston extruder. As a variant, it may be carried out in a screw extruder.

The drying step (c) is advantageously carried out at low drying rates in order to ensure that the catalyst has a high degree of cohesion. For example, predrying at low temperature (for example from room temperature to 90° C., optionally in combination with infrared or microwave irradiation) may be carried out first, the temperature may then be raised gradually in order to reach the final drying temperature. As a variant, when water can be evacuated rapidly by suitable ventilation, the temperature may be increased at a higher rate. The temperature is typically raised at a rate of 1° per minute. The drying is generally carried out at a final temperature of at least 400° C. The final drying temperature is customarily at most 500° C. Lower temperatures from 100 to 400° C. may be suitable when the drying time is long enough, for example 10 to 20 h The calcining step (d) is generally carried out at a temperature of at least 300° C., in particular at least 400° C. The temperature is customarily at most 550° C. in particular at most 520° C. Temperatures in excess of 550-C are not recommended because most titanium zeolites cannot withstand such temperatures. The duration of the calcining step (d) must be long enough to make it possible to remove most of the organic residues originating from the binder and/or the plasticizer. Durations of 60 h are typical. Generally, the duration is at least 50 h and at most 100 h. The calcining step (d) is preferably carried out in an oxidizing atmosphere, preferably in air.

As it is described above, the process comprising steps (a) to (d) and a granulation step can be used to prepare other catalysts in the form of extruded granules.

The catalyst according to the invention can be used in the synthesis of epoxides by reacting an olefinic compound with a peroxide compound.

The invention therefore also relates to the use of the catalyst described above in these syntheses.

The invention also relates to a process for the preparation of an epoxide by reacting an olefinic compound with a peroxide compound in the presence of the catalyst described above. The epoxide is preferably 1,2-epoxy-3-chloropropane or 1,2-epoxypropane. The olefinic compound is preferably allyl chloride or propylene. The peroxide compound can be chosen from those containing active oxygen and capable of carrying out epoxidations. Hydrogen peroxide and those peroxide compounds which can produce hydrogen peroxide under epoxidation reaction conditions are suitable. The peroxide compound is preferably hydrogen peroxide.

EXAMPLE

According to the Invention

In this example, extruded granules containing TS-1 were firstly prepared. They were then used in the synthesis of epichlorhydrin-(EPI) from allyl chloride (ALC) and hydrogen peroxide ($H_2O_2$).

A TS-1 powder was mixed with:
- 15.8 g of binder (a silicone resin powder of the polymethylsiloxane type with an $SiO_2$ content of 87% after calcining at 500° C.) per 100 g of TS-1,
- 4 g of plasticizer (methyl cellulose with a viscosity of 12,000 mPas, the viscosity being measured in aqueous solution at 2% by weight) per 100 g of TS-1,
- 10 g of pore-forming substance (melamine) per 10 g of TS-1,
- 60 g of water per 100 of TS-1.

The mixture was then blended at room temperature for 25 min at a rod rotation speed of 50 rpm. The paste obtained was introduced into an extruder fitted with a 1 mm die. The extrudate was dried at 120° C. for 15 h before being calcined at 500° C. for 60 h in air with a temperature gradient of 1° per minute. Having been dried and calcined, the extrudate was then cut using a granulator to a length of 3 mm. The granules obtained contain 88% by weight of TS-1 and 12% of siliceous matrix produced by the calcining of the binder.

In a looped reactor containing a bed of the catalyst obtained above (amount of TS-1 introduced=2% by weight of the reaction medium), a reaction medium containing ALC, methanol and $H_2O_2$ (at 35%) was circulated in molar proportions ALC/$H_2O_2$=2, methanol/ALC=7.8. After 2.5 h of reaction at 25° C., 89% of the amount of $H_2O_2$ employed was consumed. The selectivity with respect to EPI (the molar ratio between the amount of EPI produced and the sum of the amounts of products formed) was 99%.

What is claimed is:

1. A process for the preparation of epoxides comprising reacting an olefinic compound with a peroxide compound in the presence of an epoxidation catalyst obtained according to a process comprising:

(a) blending a mixture comprising a TS-1 titanium zeolite powder, water, at least one silicon derivative binder, at least one plasticizer in an amount of at least 1% and less than 10% by weight relative to the weight of titanium zeolite employed, a pore-forming substance and optionally other additives, in order to form a paste, said plasticizer and said pore-forming substance being distinct from one another and said pore-forming substance being added to the mixture in step (a) in an amount of from 5 to 35% by weight, compared to the weight of the titanium zeolite, and said binder being added to the mixture in step (a) in an amount of more than 5% and less than 20% by weight, compared to the weight of the titanium zeolite, (b) shaping the paste obtained in step (a) by extrusion, in order to obtain an extrudate, (c) drying in order to remove at least some of the water, and (d) calcining in order to remove at least some of the organic residues present and form pores, and comprising a granulation step carried out between the shaping step (b) and the drying step (c) or after the calcining step (d), in order to obtain extruded granules.

2. The process according to claim 1, wherein the titanium zeolite has a crystalline structure of the ZSM-5, ZSM-11, MCM-41 type, and wherein the binder is converted into a material forming a matrix of the catalyst during the calcination.

3. The process according to claim 1, wherein the titanium zeolite has an infrared absorption band at about 950-960 $cm^{-1}$.

4. The process according to claim 1, wherein the titanium zeolite is a silicalite satisfying a formula $xTiO_2(1-x)SiO_2$ in which x is from 0.0001 to 0.5.

5. The process according to claim 1, wherein the extruded granules are cylindrical and have a diameter of from 0.5 to 5 mm, and a length of from 1 to 8 mm.

6. The process according to claim 1, wherein the catalyst contains from 1 to 99% by weight, of titanium zeolite, the remainder consisting of a matrix.

7. The process according to claim 1, wherein the plasticizer is a polysaccharide and the binder comprises a siloxane derivative.

8. The process according to claim 1 wherein the titanium zeolite powder employed in step (a) has a mean diameter of less than or equal to 10 μm.

9. The process according to claim 7, wherein the polysaccharide is a cellulose selected from the group consisting of methyl cellulose, carboxymethyl cellulose and hydroxyethyl cellulose and the silicon derivative comprises a siloxane.

10. The process according to claim 1, wherein the pore-forming substance comprises melamine.

11. A process for the preparation of an epoxide selected from the group consisting of 1,2-epoxy-3-chloropropane and 1,2-epoxypropane, comprising reacting an olefinic compound selected from the group consisting of allyl chloride and propylene, with hydrogen peroxide, in the presence of an epoxidation catalyst obtained according to a process comprising:

(a) blending a mixture comprising a TS-1 titanium zeolite powder, water, at least one silicon derivative binder, at least one plasticizer in an amount of at least 1% and less than 10% by weight relative to the weight of titanium zeolite employed, a pore-forming substance and optionally other additives, in order to form a paste, said plasticizer and said pore-forming substance being distinct from one another and said pore-forming substance being added to the mixture of step a) in an amount from 5 to 35% by weight, compared to the weight of the titanium zeolite, and said binder being added to the mixture in step (a) in an amount of more than 5% and less than 20% by weight, compared to the weight of the titanium zeolite, (b) shaping the paste obtained in step (a) by extrusion, in order to obtain an extrudate, (c) drying in order to remove at least some of the water, and (d) calcining in order to remove at least some of the organic residues present and form pores, and comprising a granulation step carried out between the shaping step (b) and the drying step (c) or after the calcining step (d), in order to obtain extruded granules.

12. The process according to claim 1, wherein the pore-forming substance is added to the mixture of step (a) in an amount of from 6 to 14% by weight.

13. The process according to claim 1, wherein in step (a), the pore-forming substance is added to the mixture in an amount from 5 to 20% by weight, compared to the weight of the titanium zeolite.

14. The process according to claim 1, wherein in step (a), the pore-forming substance is added to the mixture in an amount from 5 to 14% by weight, compared to the weight of the titanium zeolite.

15. The process according to claim 11, wherein in step (a), the pore-forming substance is added to the mixture in an amount from 5 to 20% by weight, compared to the weight of the titanium zeolite.

16. The process according to claim 11 wherein in step (a), the pore-forming substance is added to the mixture in an amount from 5 to 14% by weight, compared to the weight of the titanium zeolite.

* * * * *